United States Patent
Cech et al.

(10) Patent No.: US 8,414,905 B2
(45) Date of Patent: Apr. 9, 2013

(54) FILM COATING COMPOSITIONS BASED ON POLYVINYL ALCOHOL-POLYETHER GRAFT COPOLYMER/POLYVINYL ALCOHOL COMBINATIONS WITH AN IMPROVED MOISTURE BARRIER EFFECT

(75) Inventors: Thorsten Cech, Biblis (DE); Verena Geiselhart, Heddesheim (DE); Thorsten Agnese, Ludwigshafen (DE)

(73) Assignee: BASF SE (DE)

(*) Notice: Subject to any disclaimer, the term of this patent is extended or adjusted under 35 U.S.C. 154(b) by 194 days.

(21) Appl. No.: 12/970,113

(22) Filed: Dec. 16, 2010

(65) Prior Publication Data

US 2011/0142888 A1 Jun. 16, 2011

Related U.S. Application Data

(60) Provisional application No. 61/286,866, filed on Dec. 16, 2009.

(51) Int. Cl.
- *A61K 9/00* (2006.01)
- *A61K 9/48* (2006.01)
- *A61K 9/28* (2006.01)
- *A61K 47/00* (2006.01)

(52) U.S. Cl.
USPC ......... 424/400; 424/463; 424/474; 514/772.2

(58) Field of Classification Search .............. 424/463, 424/400, 474; 514/772.2
See application file for complete search history.

(56) References Cited

U.S. PATENT DOCUMENTS

| | | | |
|---|---|---|---|
| 6,579,953 B1 | 6/2003 | Gotsche et al. | |
| 2005/1010749 | 5/2005 | Kolter et al. | |
| 2008/0044469 A1* | 2/2008 | Kolter et al. | 424/463 |

FOREIGN PATENT DOCUMENTS

| | | |
|---|---|---|
| DE | 1077430 B | 3/1960 |
| DE | 1081229 B | 5/1960 |
| DE | 1094457 B | 12/1960 |
| EP | 2106789 A1 | 10/2009 |
| EP | 2106789 A1 | 10/2009 |
| GB | 922457 | 4/1963 |
| GB | 922458 A | 4/1963 |
| GB | 922459 A | 4/1963 |
| WO | WO-00/18375 A1 | 4/2000 |
| WO | WO-01/04195 A1 | 1/2001 |
| WO | WO-03/070224 A1 | 8/2003 |
| WO | WO-2006/002808 A2 | 1/2006 |

OTHER PUBLICATIONS

Bühler, "Polyvinylpyrrolidone Excipients for Pharmaceuticals", pp. 214-216, (2005).
International Search Report for PCT/EP2010/069556.

* cited by examiner

*Primary Examiner* — Blessing Fubara
(74) *Attorney, Agent, or Firm* — Novak Druce Connolly Bove + Quigg LLP

(57) ABSTRACT

Film coating compositions based on a co-processed mixture of a polyvinyl alcohol-polyether graft polymer and polyvinyl alcohol (component A), a N-vinylpyrrolidone-vinyl acetate copolymer (component B) and pigments (component C).

20 Claims, 2 Drawing Sheets

Example: 1-5

Example: 1 - 5

Example: 6 - 10

Example: i - v

FILM COATING COMPOSITIONS BASED ON POLYVINYL ALCOHOL-POLYETHER GRAFT COPOLYMER/POLYVINYL ALCOHOL COMBINATIONS WITH AN IMPROVED MOISTURE BARRIER EFFECT

CROSS-REFERENCE TO RELATED APPLICATIONS

This application claims the benefit of U.S. Provisional Application 61/286,866 filed on Dec. 16, 2009.

BACKGROUND OF THE INVENTION

The present invention relates to film coatings for the coating of dosage forms of pharmaceutical or dietetic active ingredients or nutritional supplements, where the film coating compositions consist of a co-processed mixture of polyvinyl alcohol-polyether graft copolymer and polyvinyl alcohol (component A) and a vinylpyrrolidone-vinyl acetate copolymer (component B), organic or inorganic pigments (components C), optionally a surfactant, preferably a surfactant with an HLB value greater than 10 (component D) and further customary coating constituents. The film coatings are preferably intended to be used for instant-release coatings.

Solid administration forms are provided with a rapidly soluble coating for very different reasons. In this way, for example, it is possible to improve the appearance, the differentiability and the swallowability, to conceal a bitter taste or to protect the administration form against external influences such as e.g. moisture or oxygen. Since the film coating should dissolve rapidly in various aqueous media including in artificial gastric and intestinal juice, the most important constituent of the coating preparation has to be a water-soluble, film-forming polymer. For the coating of tablets, the film-forming polymers used are primarily hydroxypropylmethylcellulose and hydroxypropyl-cellulose, although these have serious disadvantages. For example, the viscosity of these polymers in water is very high and permits only a concentration up to ca. 10% since, on account of the high viscosity at relatively high concentrations, fine atomization in the spray nozzle is no longer possible and the coating becomes rough, inhomogeneous and unappealing. Furthermore, these polymers are very brittle and often suffer cracks during storage, particularly if the core alters its volume due to moisture absorption or release.

The use of polyvinyl alcohol-polyether graft copolymers as coating compositions or binders in pharmaceutical administration forms or as packaging material or as additive in cosmetic, dermatological or hygiene preparations is known, for example, from WO 00/18375. Thus, for example, a formulation for a film coating composition is described which consists of a polyvinyl alcohol-polyether graft copolymer and the customary coating constituents for coloring and covering, namely iron oxide, talc and titanium dioxide. Although a coating of this type is flexible, it is relatively soft and exhibits abrasion phenomena when shear forces act upon it. This plays a role particularly in the case of very large coating batches because then the high pressure caused by the large charge of the tablets in conjunction with the rolling movement of the tablets in the drum accordingly produces high shear forces. Since many medicaments and also some auxiliaries are very lipophilic, the coatings often do not adhere well to the tablet surface. Moreover, smoothness and shine of such film coating compositions are often unsatisfactory.

Polyvinyl alcohol is likewise known as film former, but is rarely used on account of various disadvantages. The use of polyvinyl alcohol-containing preparations which consist of polyvinyl alcohol, plasticizers and talc is described in WO 01/04195. Disadvantages of these preparations are the slow dissolution during the preparation of the aqueous coating solution, the high viscosity, the low concentration in the spraying solution, the use of plasticizers and the slow dissolution rate of the film coating, especially after storage, and also an embrittlement of the film coating following storage accompanied by cracking. Moreover, the spraying of relatively highly concentrated polyvinyl alcohol solutions (>8%) leads to thread formation at the spray nozzle.

The copolymers also referred to in the pharmacopoeia as copolyvidone or copovidone and obtained from N-vinylpyrrolidone and vinyl acetate in the weight ratio 60:40 is likewise known as film formers. Since the water absorption of copovidone is comparatively high, copovidone on its own is rarely suitable as film former and is usually combined with less hygroscopic substances in order to improve the brittleness and solubility of the film coatings. It is also mentioned that copovidone can be used as subcoating in order to protect tablet cores with moisture-sensitive active ingredients prior to the application of aqueous coating solutions or film coatings. (cf. V. Bühler, "Polyvinylpyrrolidone Excipients for Pharmaceuticals", pp. 214-216, Springer Verlag Berlin Heidelberg 2005). However, copovidone on its own can only be applied as intermediate layer from an organic solution.

Pigments are an essential constituent of film coatings. In the film coating, they serve not only for coloring purposes, but can also develop a certain barrier effect. However, relatively high pigment contents in the film coating composition are disadvantageous from the point of view of application since, on the one hand, the incorporation of relatively high pigment fractions into an aqueous spray suspension is complicated, and, on the other hand, the spraying of suspensions with a high pigment content is also more difficult to control. Added to this is the fact that spray suspensions with a high pigment content have a greater tendency toward separation.

WO 03/070224 describes coatings which consist of polyvinyl alcohol-polyether graft copolymers, a component with hydroxy, amide or ester functions and further customary coating constituents. Here, firstly a premix of the feed substances is prepared as physical mixture and this is then dispersed in water. These preparations have a tendency toward separation and do not have good roughness values.

WO 2006/002808 describes rapidly dispersible film coating compositions based on polyvinyl alcohol-polyether graft polymers which, on account of particularly finely divided pigments, have a low roughness and good physical stability. Also described are combinations of two polymers such as, for example, a two-component combination of the graft polymer with a vinylpyrrolidone-vinyl acetate 6:4 copolymer. However, limits are imposed on such coating compositions for the pigment loading. The water-vapor permeation is also still not satisfactory in the case of such films.

In principle, film coatings with a high pigment loading of as far as possible 50% by weight or more are desired. However, film coating compositions with a relatively high pigment loading that are known hitherto do not meet the requirements for water-vapor permeation.

BRIEF SUMMARY OF THE INVENTION

It was an object of the invention to find improved film coating compositions which have improved moisture protection for the active ingredient. Such film coating compositions should be as rapidly dissolvable in water as possible and thus be suitable for instant-release forms. Moreover, the film coatings should be optimized with regard to their pigment loading. The coating compositions, even in powder form, should have a tendency toward no kind of separation between the individual constituents, especially not toward separation between pigments and polymers, and should, furthermore, be excellently flowable.

Accordingly, film coating compositions based on a co-processed mixture of a polyvinyl alcohol-polyether graft polymer and polyvinyl alcohol (component A), an N-vinylpyrrolidone-vinyl acetate copolymer with a weight ratio of 6:4 (component B), pigments (component C), optionally surfactants (component D) and optionally further pharmaceutical auxiliaries (components E) have been found.

The film coating compositions can be composed as follows:
A) 10-75% by weight of a co-processed mixture of polyvinyl alcohol-polyether graft copolymers and polyvinyl alcohol (component A),
B) 5-45% by weight of a polyvinylpyrrolidone or of a vinylpyrrolidone-vinyl acetate copolymer (component B)
C) 10-85% by weight of pigments (component C)
D) 0-10% by weight of one or more surfactants (component D) and
E) 0-30% by weight of further customary coating constituents (components E),
where the amount of components A to E adds up to 100% by weight.

A BRIEF DESCRIPTION OF THE FIGURES

DETAILED DESCRIPTION OF THE INVENTION

Figure 1:
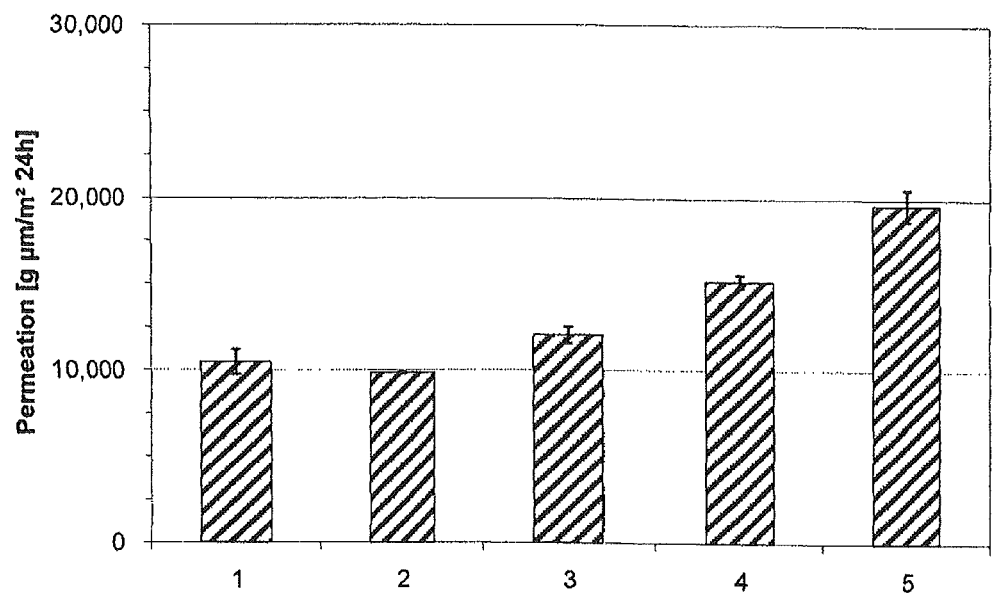
FIG. 1 illustrates the results of the permeation measurements for the water-vapor permeation for examples 1-5.

Component A is a co-processed mixture of a polyvinyl alcohol-polyether graft copolymer and polyvinyl alcohol.

Polyvinyl alcohol-polyether graft copolymers are understood as meaning polymers obtainable by polymerization of at least one vinyl ester of aliphatic $C_1$-$C_{24}$-carboxylic acids, preferably vinyl acetate, in the presence of polyethers as graft base and subsequent complete or partial saponification of the polyvinyl ester groups.

Preference is given to polyethers with an average molecular weight between 400 and 50 000 g/mol, particularly preferably 1500 to 20 000 g/mol.

The preparation of such graft copolymers is known per se.

DE 1 077 430 describes a process for the preparation of graft polymers of vinyl esters on polyalkylene glycols.

DE 1 094 457 and DE 1 081 229 describe processes for the preparation of graft polymers of polyvinyl alcohol on polyalkylene glycols by saponification of the vinyl esters and their use as protective colloids, water-soluble packaging films, as sizing and finishing agents for textiles and in cosmetics.

Preference is given to polymers with a degree of saponification of the polyvinyl ester groups of >70 mol %, particularly preferably >80 mol % and very particularly preferably of >85 mol %.

Particular preference is given to a polyvinyl alcohol-polyether graft copolymer in which vinyl acetate has been used as monomer to be grafted and polyethylene glycol 6000 has been used as graft base, and the degree of saponification of the ester groups is >85 mol %, where the mass ratio of the molecular moieties polyvinyl alcohol/polyethylene glycol 6000 is 75:25.

Polyvinyl alcohol is understood as meaning a by homopolymer which is usually obtained by polymerization of vinyl acetate and saponification of the acetate groups. Suitable polyvinyl alcohols preferably have a degree of hydrolysis (degree of saponification of the acetate group) of >80 mol %, preferably >85 mol %. The viscosities of a 4% strength by weight aqueous solution at 20° C. can be 3 to 30, preferably 3 to 20 mPas.

Graft polymer and polyvinyl alcohol are co-processed, so that an intimate mixture of the individual components is present. On account of the preparation process, the individual components are embedded in one another, meaning that they do not separate and the embedding can no longer be separated using mechanical means. Component A is prepared through the joint spraying of an aqueous solution of the polymers. Preferably, component A also comprises silicon dioxide. A particularly preferred component A consists of 55-65% by weight of graft polymer, 35 to 45% by weight of polyvinyl alcohol and 0.1 to 0.3% by weight of silicon dioxide.

Component A is preferably present in amounts of from 15 to 60% by weight, particularly preferably 20 to 45% by weight.

Furthermore, the film coating compositions comprise, as components B, a copolymer known from the pharmacopoeia as copolyvidone or copovidone, which is obtained from vinylpyrrolidone and vinyl acetate in the weight ratio 60:40. The K value in accordance with Fikentscher, measured at 1% strength by weight in water, of these polymers is in the range from 20 to 50, preferably 25 to 35. Components B are preferably present in amounts of from 5 to 35% by weight, particularly preferably from 5 to 20% by weight.

Furthermore, the film coating compositions comprise, as components C, organic or inorganic pigments.

Pigments is the term used to refer to color-imparting or white substances which are insoluble in the application medium. The pigments may be inorganic or organic pigments.

Suitable inorganic pigments are aluminum silicates, magnesium silicates, magnesium aluminum silicates, iron oxide, titanium dioxide, zinc oxide, silica, or calcium hydrogen phosphate. Among the aluminum silicates, kaolin is primarily suitable. Among the magnesium silicates, talc in particular is of importance.

Preferred pigments are iron oxide and white pigments selected from the group consisting of titanium dioxide, talc and kaolin.

Suitable organic pigments are organic colored lakes or mixtures thereof. Organic colored lakes which can be used are e.g. quinoline yellow lake, tartrazine lake, yellow orange lake, FD&C yellow aluminum lake, cochineal red lake, erythrosine lake, azorubine lake, indigotin lake, betacarotene.

The pigments are preferably present in amounts of from 20 to 75% by weight.

As components D, if desired, surfactants can be used, preferably surfactants with an HLB value greater than 10 (HLB value: Hydrophilic Lipophilic Balance; cf. Fiedler, Lexikon der Hilfsstoffe [Lexicon of Auxiliaries], Editio Cantor Verlag Aulendorf, 5th edition (2002), pages 115-121) greater than 10 are used. If surfactants are used, then they may be used in amounts of from 0.1 to 10% by weight, preferably 1 to 5% by weight.

Of particular suitability are alkali metal salts of C8-C30-fatty acids, C8-C30-alkylsulfonates, C8-C30-alkylsulfates, C8-C30-alkylarylsulfonates or dioctyl sulfosuccinate, ethoxylates of C8-C30-fatty acids, C8-C30-fatty alcohols, fatty acid glycerides, sorbitan fatty acid esters, sorbitan fatty alcohol ethers or phenols, and also polyoxypropylene-polyoxyethylene block copolymers. Examples from the specified substance classes are sodium stearate, sodium oleate, sodium laurylsulfonate, sodium lauryl sulfate, polyoxyethylene(9) monostearate, polyoxyethylene(10) stearyl cetyl ether, polysorbate 80, polysorbate 20, ethoxylated castor oil (35 EO), ethoxylated hydrogenated castor oil (40 EO), ethoxylated 12-hydroxystearic acid (15 EO), poloxamer 188, poloxamer 408.

In addition, the film coatings can comprise, as components E, additional auxiliaries as are customary as coating constituents. Further customary coating constituents comprise:

water-soluble dyes, detackifiers, fillers, gloss improvers, foam preventers, protective colloids, buffer substances, pH-regulating substances or adhesion promoters.

The film coating compositions according to the invention can firstly be prepared as white preparation, to which subsequently further pulverulent color-imparting components can be added. The positive properties of the film coatings are also retained during this procedure.

The preparations according to the invention usually require no plasticizer. Freedom from plasticizer is an enormous advantage because plasticizers often lead to problems during the storage of coated forms. For example, the plasticizer can migrate into the core and alter the physical and chemical properties of the active ingredient, the film becomes brittle as a result and has a tendency to crack. Moreover, most plasticizers have a certain volatility which likewise leads to embrittlement. However, if desired, an addition of plasticizer is possible.

The film coating compositions can be prepared, for example, by firstly dissolving components A and B in water. This solution can then be combined with an aqueous pigment suspension. The pigment suspension can be obtained by homogenizing the pigments, if appropriate with the addition of surface-active substances, in water.

Furthermore, all of the feed substances can also be introduced together into water and homogenized. In the case of this procedure, the use of an antifoam may also be advisable.

The amount of water used in the case of the described procedures is chosen such that the resulting aqueous dispersions of the film coating compositions according to the invention have solids contents of from 5 to 45, preferably 15 to 30% by weight.

The aqueous film coating compositions can also be converted to dry powders. The drying of the aqueous dispersions can take place in a spray drier, paddle drier or fluidized-bed drier. As a rule, the dispersion to be dried is atomized by means of pressure and dried by means of warm air. For atomization of the suspension during drying, pressures greater than 0.1 MPa, preferably greater than 2.0 MPa, particularly preferably greater than 8.0 MPa, are applied. The atomization can take place by means of single-material nozzles, dual-material nozzles or by means of rotating disks. The drying can take place at inlet-air temperatures of 50-200° C., preferably at 80-180° C.

The film coating compositions according to the invention can be obtained as powders or granules with average particle sizes of from 5 μm to 1000 μm. If desired, the particle size can also be adjusted by means of grinding processes.

For application as powders, the preparations according to the invention can be stirred into water, if appropriate admixed with further additives, in particular color-imparting additives, and be applied to the substrate by means of a suitable spraying device, in which case the film coating can be successively dried by introducing heated air. For redispersion of the pulverulent film coating compositions, no high-shear stirring tools are usually required, but merely simple low-speed stirrers.

The film coating can be applied in all coating devices suitable for solid pharmaceutical administration forms and nutritional supplements, such as, e.g. horizontal drum coaters, fluidized-bed coaters, immersion blade coaters, coating pans.

For the atomization of the coating preparation, a dual-material nozzle is preferably used. The inlet-air temperature should be between 20-90° C., preferably between 30-70° C.

In principle, all core forms with domed, convex or concave surface can be coated, irrespective of whether they are round, polygonal, oblong shapes or football shapes.

The core may also carry a subcoating, which is generally applied in order to additionally protect the active ingredient, e.g. against oxygen, protons or chemical substances of the coating and also of the stomach and intestine contents.

A further film coating, which differs in its composition, may also be applied to the film coating according to the invention. Thus, for example, a colorless film coating or a particular gloss layer can be applied.

As regards the active ingredients, there are no limitations for the dosage forms according to the invention. It is possible to use active ingredients from all areas of indication, human medicaments and animal medicaments, vitamins, carotenoids, nutraceuticals, dietetic active ingredients or nutritional supplements, mineral substances, micronutrients etc. The active ingredients may have different physicochemical properties such as lipophilicity, solubility, particle size, particle structure, surface etc.

The administration forms to be coated may be present as tablets, capsules or extrudates.

The film coating compositions according to the invention have improved properties with regard to water-vapor permeation. This is advantageous particularly with regard to moisture-sensitive active ingredients.

EXAMPLES

Unless stated otherwise, the percentages refer to % by weight.

Feed Substances (A) component A: co-sprayed mixture of 60% by weight of a polyvinyl alcohol-polyethylene glycol 6000 graft polymer (weight ratio PVA:PEG 75:25, degree of saponification 94 mol %), 40% by weight of polyvinyl alcohol (Mowiol® 5-88, Kuraray, viscosity in accordance with DIN 53015 at 5-6 mPas) and 0.2% by weight of silicon dioxide, based on the total amount of PVA-PEG and PVA, (Kollicoat® Protect, BASF)

(B) component B: copolymer of 60% by weight of N-vinylpyrrolidone and 40% by weight of vinyl acetate (copovidone), (Kollidon® VA 64, BASF SE)

SDS: sodium lauryl sulfate

Preparation of the Spray Suspension—General Procedure

Components A and B were dissolved in water with stirring to give a 20% strength by weight solution. The pigments were homogenized with water in an Ultra-Turrax mixer to give a pigment suspension with a solids fraction of 20% by weight. The pigment suspension was then stirred into the solution of components A and B.

TABLE

Composition based on solid = 100% by weight

| Ex. No. | Comp. A % by wt. | Comp. B % by wt. | Comp. C pigments % by wt. | | SDS % by wt. | Permeation**) [g μm/m² 24 h] |
|---|---|---|---|---|---|---|
| | | | Talc | Sicovit red*) | | |
| 1 | 18.7 | 6.3 | 67.5 | 7.5 | — | 10459 |
| 2 | 30.0 | 10.0 | 54.0 | 6.0 | — | 9822 |
| 3 | 37.5 | 12.5 | 45.0 | 5.0 | — | 12044 |
| 4 | 45.0 | 15.0 | 36.0 | 4.0 | — | 15171 |
| 5 | 56.2 | 18.8 | 22.5 | 2.5 | — | 19676 |
| 6 | 18.7 | 6.3 | 65.5 | 7.5 | 2.0 | 19143 |
| 7 | 30.0 | 10.0 | 52.0 | 6.0 | 2.0 | 10903 |
| 8 | 37.5 | 12.5 | 43.0 | 5.0 | 2.0 | 12878 |
| 9 | 45.0 | 15.0 | 34.0 | 4.0 | 2.0 | 11020 |
| 10 | 56.2 | 18.8 | 20.5 | 2.5 | 2.0 | 13930 |

For comparison

| Ex. No. | Comp. A % by wt. | Comp. B % by wt. | Comp. C pigments % by wt. | | SDS % by wt. | Permeation [g μm/m² 24 h] |
|---|---|---|---|---|---|---|
| | | | Talc | Sicovit red | | |
| i | 25.0 | 0 | 67.5 | 7.5 | 0 | 10742 |
| ii | 40.0 | 0 | 54.0 | 6.0 | 0 | 14847 |
| iii | 50.0 | 0 | 45.0 | 5.0 | 0 | 17247 |
| iv | 60.0 | 0 | 36.0 | 4.0 | 0 | 20769 |
| v | 75.0 | 0 | 22.5 | 2.5 | 0 | 24185 |

*)Sicovit ® red 30 E 172: iron oxide, C.I. 77491, BASF SE
**)at 23° C., 85% relative humidity, measured in accordance with ATSM F-1249.

Figure 2:
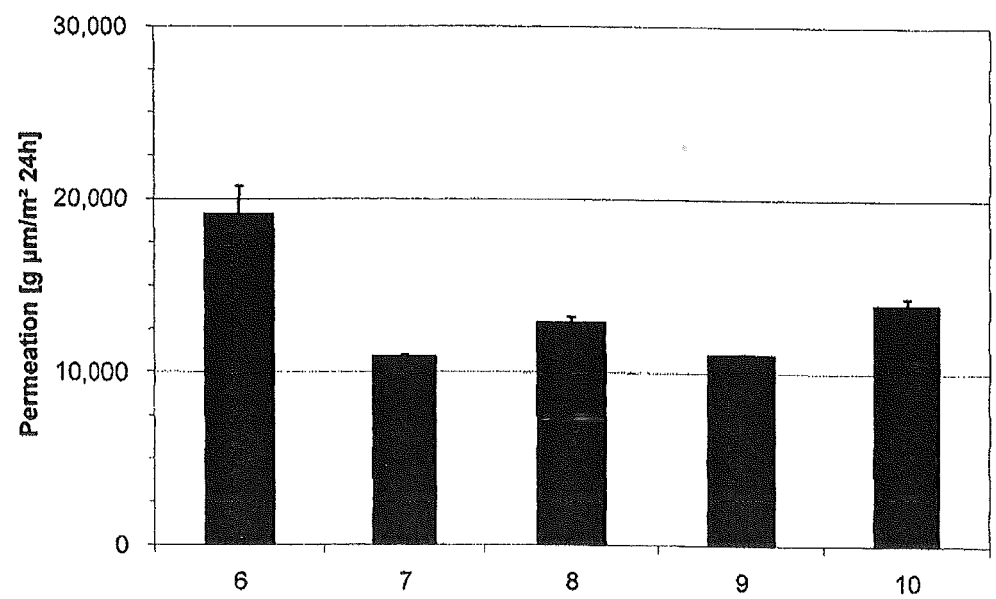
FIG. 2 illustrate the results of the permeation measurements for the water-vapor permeation for examples 6-10.
Figure 3:
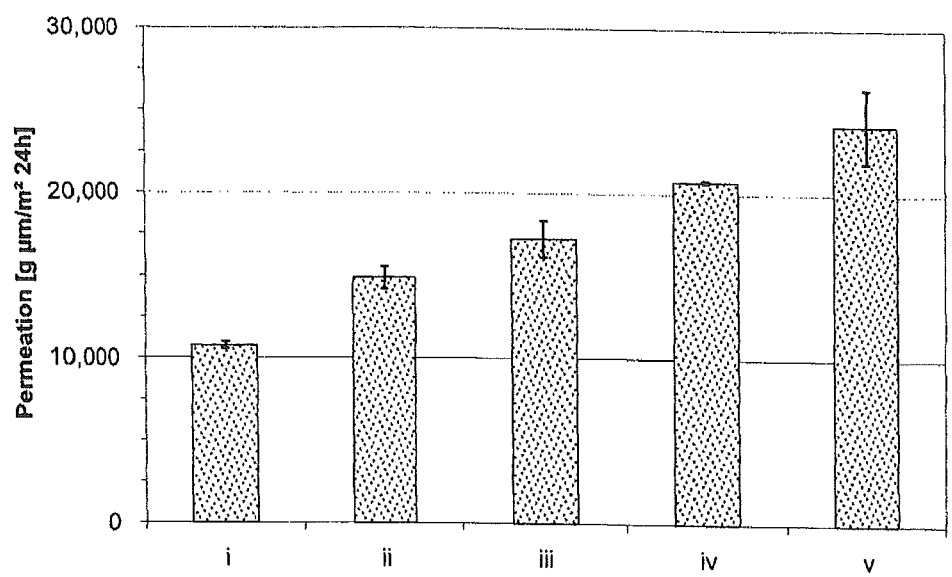
FIG. 3 illustrate the results of the permeation measurements for the water-vapor permeation for examples i-v.

The results of the permeation measurements for the water-vapor permeation are shown graphically in FIGS. 1-3.

We claim:

1. A film coating composition based on a co-processed mixture of a polyvinyl alcohol-polyether graft polymer and polyvinyl alcohol (component A), an N-vinylpyrrolidone-vinyl acetate copolymer (component B) and a pigment (component C).

2. The film coating composition according to claim 1, further comprising a surfactant (component D).

3. The film coating composition according to claim 1, further comprising further pharmaceutical auxiliaries (component E).

4. The film coating composition according to claim 1, comprising
   A) 10-75% by weight of a co-processed mixture of polyvinyl alcohol-polyether graft copolymers and polyvinyl alcohol (component A),
   B) 5-35% by weight of a vinylpyrrolidone-vinyl acetate copolymer (component B)
   C) 10-85% by weight of pigments (component C)
   D) 0-10% by weight of one or more surfactants (component D) and
   E) 0-30% by weight of further coating constituents (components E),
   where the amount of components A to E adds up to 100% by weight.

5. The film coating composition according to claim 1, comprising
   A) 15-60% by weight of a co-processed mixture of polyvinyl alcohol-polyether graft copolymers and polyvinyl alcohol (component A),
   B) 5-30% by weight of a vinylpyrrolidone-vinyl acetate copolymer (component B)
   C) 20-75% by weight of pigments (component C)
   D) 0-10% by weight of one or more surfactants (component D) and
   E) 0-30% by weight of further customary coating constituents (components E).

6. The film coating composition according to claim 1, comprising
   A) 20-45% by weight of a co-processed mixture of polyvinyl alcohol-polyether graft copolymers and polyvinyl alcohol (component A),
   B) 5-20% by weight of a vinylpyrrolidone-vinyl acetate copolymer (component B)
   C) 20-75% by weight of pigments (component C)
   D) 0-10% by weight of one or more surfactants (component D) and
   E) 0-30% by weight of further customary coating constituents (components E).

7. The film coating composition according to claim 6, wherein component A is obtained by spraying a combined solution of the polyvinyl alcohol-polyether graft polymer and of the polyvinyl alcohol,
   component B is a copolymer with a weight ratio of N-vinylpyrrolidone to vinyl acetate of 6:4,
   component C is an organic or inorganic pigment and
   component D is sodium lauryl sulfate in amount of from 1 to 5% by weight.

8. The film coating composition according to claim 1, wherein component A is a polyvinyl alcohol-polyether graft polymer obtained by polymerization of vinyl acetate in the presence of a polyether as graft base and subsequent saponification of more than 85 mol % of the acetate groups.

9. The film coating composition according to claim 1, wherein component A is a polyvinyl alcohol with a degree of hydrolysis of >80 mol %.

10. The film coating composition according to claim 1, wherein component A is obtained by spraying a combined solution of the polyvinyl alcohol-polyether graft polymer and of the polyvinyl alcohol.

11. The film coating composition according to claim 1, wherein components C is an organic pigment.

12. The film coating composition according to claim 1, wherein components C is an inorganic pigment.

13. The film coating composition according to claim 1, wherein component B is a copolymer with a weight ratio of N-vinylpyrrolidone to vinyl acetate of 6:4.

14. The film coating composition according to claim 1, wherein component D is a surfactant with an HLB value greater than 10.

15. The film coating composition according to claim 1, wherein component D is in amount of from 1 to 5% by weight.

16. The film coating composition according to claim 1, wherein component D is sodium lauryl sulfate.

17. The film coating composition according to claim 1, wherein component E is a water-soluble dye, detackifier, filler, gloss improver, foam preventer, protective colloid, buffer substance, pH-regulating substance or adhesion promoter or mixtures thereof.

18. The film coating composition according to claim 1, in the form of powders or aqueous dispersions.

19. A dosage form provided with a film coating, where the film coating is obtained by applying the film coating composition according to claim 1.

20. The dosage form as claimed in claim 19, further comprising pharmaceutical or dietetic active ingredients or nutritional supplements.

* * * * *